(12) United States Patent
Rimm et al.

(10) Patent No.: US 7,129,056 B2
(45) Date of Patent: Oct. 31, 2006

(54) METHOD FOR THE DETECTION, IDENTIFICATION, ENUMERATION AND CONFIRMATION OF VIRALLY INFECTED CELLS AND OTHER EPITOPICALLY DEFINED CELLS IN WHOLE BLOOD

(76) Inventors: David L. Rimm, 15 Pawson Landing, Branford, CT (US) 06405; Paul Fiedler, 90 Gilnock Dr., New Haven, CT (US) 06515; Robert A. Levine, 31 Pilgrim La., Guilford, CT (US) 06437; Stephen C. Wardlaw, Highrock, Lyme, CT (US) 06371

( * ) Notice: Subject to any disclaimer, the term of this patent is extended or adjusted under 35 U.S.C. 154(b) by 0 days.

(21) Appl. No.: 11/155,856

(22) Filed: Jun. 20, 2005

(65) Prior Publication Data
US 2005/0239058 A1 Oct. 27, 2005

Related U.S. Application Data

(60) Division of application No. 10/042,016, filed on Jan. 10, 2002, now Pat. No. 6,911,315, which is a continuation-in-part of application No. 09/800,344, filed on Mar. 5, 2001, now Pat. No. 6,670,197, which is a continuation-in-part of application No. 08/976,886, filed on Nov. 24, 1997, now Pat. No. 6,197,523.

(51) Int. Cl.
G01N 33/53 (2006.01)

(52) U.S. Cl. .................. 435/7.24; 435/7.2; 435/7.21; 436/63; 436/64; 436/165; 436/810

(58) Field of Classification Search ............. 435/7.2, 435/7.21, 7.24; 436/63, 64, 165, 810
See application file for complete search history.

(56) References Cited

U.S. PATENT DOCUMENTS

| | | | | |
|---|---|---|---|---|
| 4,027,660 A | * | 6/1977 | Wardlaw et al. | 600/584 |
| 4,082,085 A | * | 4/1978 | Wardlaw et al. | 600/309 |
| 4,156,570 A | * | 5/1979 | Wardlaw | 356/36 |
| 5,086,784 A | * | 2/1992 | Levine et al. | 600/584 |
| 5,198,927 A | * | 3/1993 | Rathbone et al. | 359/385 |
| 5,251,474 A | * | 10/1993 | Wardlaw et al. | 73/61.41 |
| 5,252,460 A | * | 10/1993 | Fiedler et al. | 435/7.22 |
| 5,321,975 A | * | 6/1994 | Levine et al. | 73/61.71 |
| 5,342,790 A | * | 8/1994 | Levine et al. | 436/523 |
| 5,349,468 A | * | 9/1994 | Rathbone et al. | 359/390 |
| 5,393,674 A | * | 2/1995 | Levine et al. | 436/177 |
| 5,403,714 A | * | 4/1995 | Levine et al. | 435/7.2 |
| 5,460,979 A | * | 10/1995 | Levine et al. | 436/523 |
| 5,496,704 A | * | 3/1996 | Fiedler et al. | 435/7.22 |
| 5,593,848 A | * | 1/1997 | Levine et al. | 435/7.24 |
| 5,635,362 A | * | 6/1997 | Levine et al. | 435/7.24 |
| 5,707,876 A | * | 1/1998 | Levine | 436/177 |
| 5,759,794 A | * | 6/1998 | Levine et al. | 435/7.24 |
| 5,776,710 A | * | 7/1998 | Levine et al. | 435/7.24 |
| 5,834,217 A | * | 11/1998 | Levine et al. | 435/7.24 |
| 6,444,436 B1 | * | 9/2002 | Rimm et al. | 435/40.51 |
| 6,911,315 B1 | * | 6/2005 | Rimm et al. | 435/7.22 |

* cited by examiner

Primary Examiner—Christopher L. Chin
(74) Attorney, Agent, or Firm—William W Jones

(57) ABSTRACT

A method for analyzing blood enables one to isolate, detect, enumerate and confirm under magnification the presence of target cells which have expressed surface epitopes that indicate intracellular infection by various viruses or other infectious agents, and also cells which have expressed surface epitopes that indicate the presence of non-infectious medical conditions. The analysis involves the examination of cells in the blood sample for the presence or absence of particular surface epitopes while the blood sample is disposed in a centrifuged blood sampling container. The epitopic analysis for the presence or absence of infected cells, or cells which indicate the presence of non-infectious medical conditions relies on the detection of known target expressed epitopes. The target epitopes on the target cell types are epitopes which are also known to be absent on normal circulating cells in the blood. Fluorophores or other labels with distinct wavelength emissions are coupled with specific binding agents such as lectins, antibodies, aptamers, or the like, which are directed against the target expressed epitopes. The epitopic analyses may be performed in or near the expanded buffy coat layer in the centrifuged blood sample. The epitopic analysis may be performed under magnification either visually and/or photometrically. The blood sampling container is sized to hold between about 1 and about 20 ml, preferably about 10 ml of blood, and contains an insert that occupies about 90–98% of the volume of the container bore in the area of the container where the target cells will, if present, be detected. The insert forces the target cells in question to reside in an annular space in the container which is adjacent to the circumference of the container bore. The entire analysis can be performed in a relatively short period of time which is typically a matter of minutes to single digit hours.

3 Claims, 2 Drawing Sheets

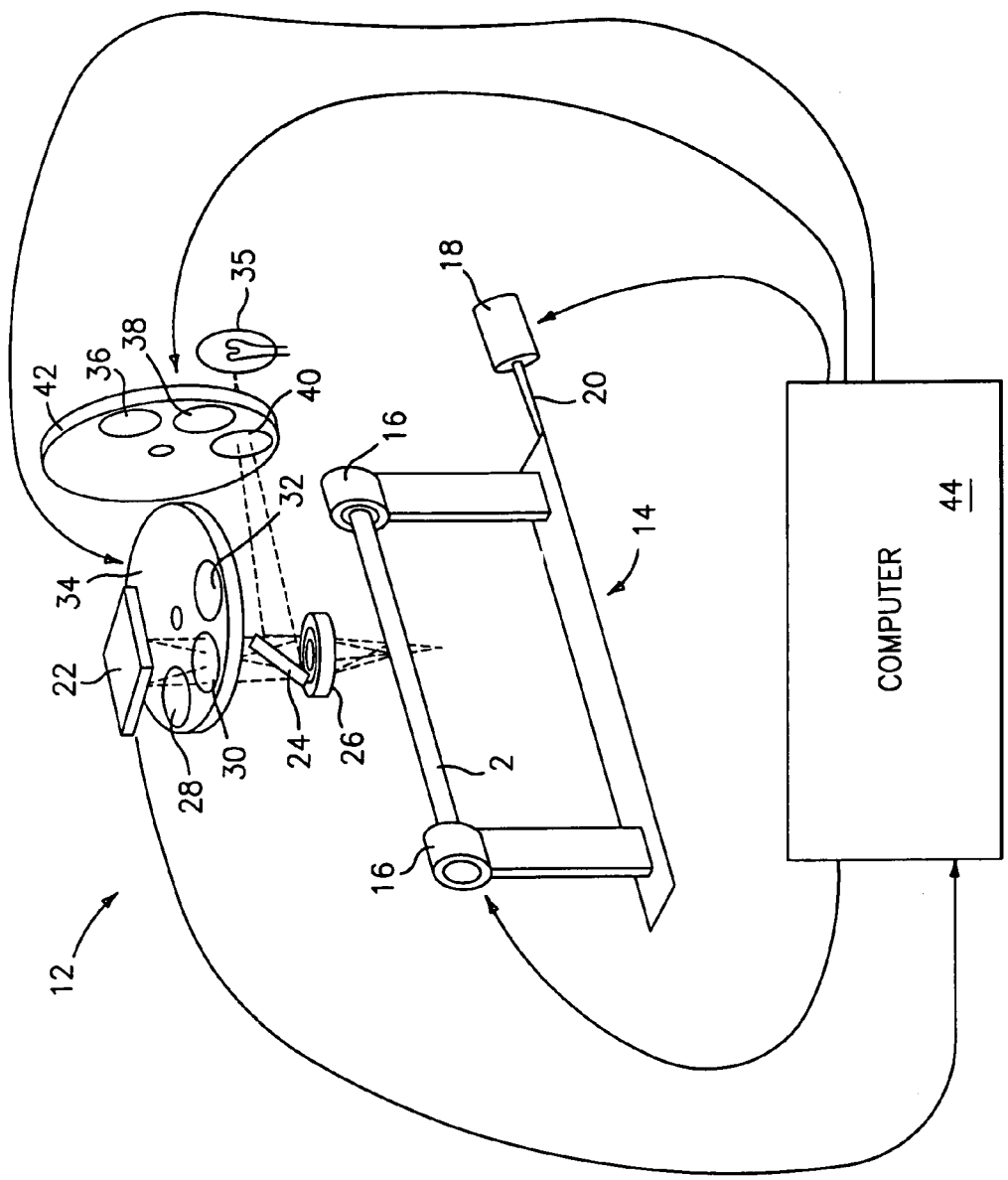
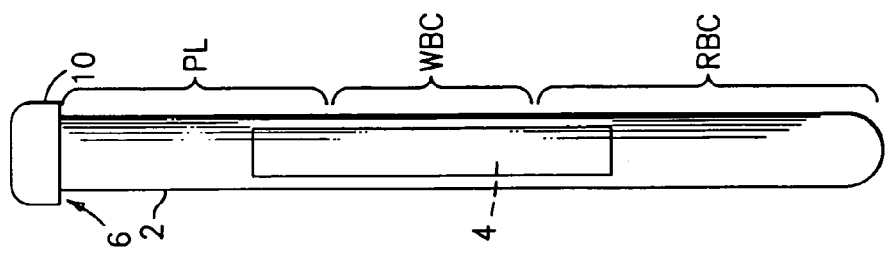
FIG. 1
FIG. 2

METHOD FOR THE DETECTION, IDENTIFICATION, ENUMERATION AND CONFIRMATION OF VIRALLY INFECTED CELLS AND OTHER EPITOPICALLY DEFINED CELLS IN WHOLE BLOOD

This is a division of patent application USSN 10/042,016, filed Jan. 10, 2002, U.S. Pat. No. 6,911,315.

This is a continuation-in-part of U.S. Ser. No. 09/800,344, filed Mar. 5, 2001 now U.S. Pat. No. 6,670,197, which, in turn, is a continuation-in-part of U.S. Ser. No. 08/976,886, filed Nov. 24, 1997, now U.S. Pat. No. 6,197,523.

TECHNICAL FIELD

This invention relates to a method and assembly for the detection, identification, enumeration and confirmation of virally or non-virally infected cells, or other cells which, due to the presence of expressed epitopes, indicate other particular medical conditions. The procedure of this invention is performed in a centrifuged anticoagulated whole blood sample, which sample is contained in a transparent sampling container assembly. The detection, identification, enumeration and confirmation steps can all be performed in situ in the sampling container assembly. More particularly, the method of this invention involves the centrifugal density-based separation of the contents of the blood sample and the detection in the blood sample of labeled particular expressed target surface epitopes on target cells which epitopes indicate the presence of a particular medical condition, which may or may not be disease-related. In any case, the epitopes will be surface proteins which are expressed on the target cells in question due to the presence of an infection, or another particular medical condition. The target cells in question could be lymphocytes, monocytes, granulocytes, nucleated red blood cells, or the like.

BACKGROUND ART

A number of viruses are clinically important to be able to accurately detect in blood. Specifically, HIV, CMV (cytomegalovirus), HCV (hepatitis C virus) and EBV (Epstein-Barr virus), are all currently detected using PCR-based or serologic tests. The market for these tests, especially HIV viral load, is immense. PCR is sensitive and quantitative, but is very expensive and imprecise in that it may detect contaminants or other cross-reacting sequences in the sample, if not done correctly. Serology does not provide quantitative information, i.e., how much of the virus is present?

There exists a compelling need for a simple procedure and a system for performing such a procedure whereby a sample of blood could be quickly and accurately analyzed for the number of infected cells, or other medical condition-indicative cells, which cells are distinguished by expressed proteins (epitopes) which result from the infection or other medical condition, and are not found on other cells. Additionally, the procedure should enable one to differentiate such cells from other cells, all in situ, in the blood sampling paraphernalia in a relatively short period of time.

DISCLOSURE OF THE INVENTION

This invention relates to a method for visually or photometrically detecting the presence or absence, and/or enumerating the number, of circulating infected or other medical condition-indicative cells in an anticoagulated whole blood sample, which blood sample is contained in a transparent sampling container. By "infected cells" we mean cells, typically lymphocytes, monocytes and/or granulocytes which are found in the blood sample, which infected cells have been epitopically altered by means of intracellular viral infections, or by means of intracellular non-viral infections. The detection and confirmation of circulating infected cells in the blood sample can be made in a relatively short time in situ in the sampling container. The blood sample being tested is preferably a relatively high volume sample of about 10 ml, which is contained in an assembly which may include a container and an internal insert of the type described is co-pending U.S. patent application Ser. No. 09/507,635, filed Feb. 22, 2000. The container can be a relatively flat container as shown in the aforesaid patent application, or it can be a cylindrical container. The shape of the insert will mimic the shape of the interior of the container. The container should be sufficiently large to be able to detect the target cells, which may be referred to as "rare events" in that they may occur in the blood in a concentration as low as 10–100 cells per 10 mls of blood. Thus, the preferred size of the container is such that it will hold 10 mls of a sample of blood to be analyzed.

This invention provides for the analyses of blood that fills a niche between the flow cytometer and the blood smear, or devices that do automated analysis of blood smears like the Compucyte Laser Scanning Cytometer or the Chromavision ACIS device. This invention is superior in enumerating rare events (10–100 targets/10 ml sample) when-compared to flow cytometry, which is very weak in these application areas when used without an enrichment procedure. Similarly it will enable the analysis of substantially more sample volume than the blood smear slide-based procedures. This invention enables blood sample analyses which include the detection of intracellular viral infestation and enumeration of disease-indicative blood cells or fragments of such blood cells based on abnormal epitopes which are expressed onto the cell membranes due to the diseased nature of the cells, or also to detect other cells which have surface epitopes which are not normally found in mammalian blood cells.

The tests could be performed by using antibodies that detect surface antigens on cells (generally lymphocytes/monocytes and/or granulocytes) that are infected with viruses. The literature shows ample evidence of virus-specific proteins being expressed onto the surface of lymphocytes that are antigenically available. Any type of cell having epitopic distinctions could be detected and counted using the procedure of this invention. As used in this specification, the phrase "target cells" means "cells having expressed surface antigens which indicate the presence of a particular target biological condition in the blood donor". For example, this invention may have value in evaluation of graft vs. host disease wherein target cells expressing HLA antigens from the graft could be measured in the blood. It might also be used to detect target fetal cells in the maternal blood based on paternally derived surface antigens. The target cells can be generally characterized as blood cells which have surface epitopes that are not normally found on a subject's blood cells. The surface epitopes are expressed onto the cell membrane as a result of some condition which exists inside of the cells in question. The same types of blood cells which do not have the internal condition will not have the expressed surface epitopes in question, and thus are not "target cells".

This invention allows in situ, i.e., in the sampling paraphernalia, visual or automated epitopic analysis and identification of target cells which have unique proteins expressed on their surface as a result of an alteration of the cells in question by a virus or some other infection, or other cellular abnormality-indicative condition. The invention also can allow in situ analysis and enumeration of the highlighted target cells in the sampling tube assembly. Such analysis can confirm whether individual highlighted target cells are infected, and if so, what they are infected by, all without removing the blood sample from the sampling tube.

The target cells in question may be found in or near the buffy coat area of the centrifuged blood sample, when the blood sample is examined under appropriate magnification.

In order to detect target cells the blood sample will admixed with a solution containing labeled target epitope-specific binding materials. The epitopic labels, depending upon their nature, will maximally fluoresce at different wavelengths, thus allowing the detection of target cells visually or by means of an automated instrument. Binding materials with different labels may be employed so that target cells may be classified as label A (+) and/or A (−) and label B (−) and/or B (+), in a Boolean manner. In such cases, a number of sets of different distinguishing wavelength signal emissions can be acquired. For example, the centrifuged blood sample can be scanned by an appropriate instrument so as to identify all labeled target cells. The visual. analysis, or the photometric analysis, may be performed in the vicinity of the expanded buffy coat in the blood sample, or in other areas of the blood sample where the target cells are expected to settle during centrifugation of the blood sample. The labels in question will be attached to antibodies or other binding materials which are directed against the target epitopes. Any non-bound label will diffuse into the blood sample after the appropriate incubation period and will end up in the plasma after centrifugation of the blood sample.

It is therefore an object of this invention to provide a method and apparatus for detecting, identifying and confirming the presence or absence of target blood cells in a centrifuged anticoagulated whole blood sample which is contained in a transparent container.

It is an additional object of this invention to provide a method and apparatus of the character described wherein the target cells are highlighted and differentiated from non-target cells in the blood sample.

It is a further object of this invention to provide a method and apparatus of the character described wherein a labeled target cell detection step can be performed either visually or by an appropriate photodetector.

It is a further object of this invention to provide a method and apparatus of the character described which enables enumeration of target blood cells in the blood sample.

It is another object of this invention to provide a method and apparatus of the character described wherein the blood sample analysis is performed in situ in a closed system which system is resistant to contamination from ambient surroundings, thereby reducing the possibility of false positive results, and which also protects laboratory workers from contamination from the sample.

It is yet another object of this invention to provide a method and apparatus for detecting, by Boolean logic, the identity of target cells by the presence or absence of more than one differentially detectable labeled binding agents which are directed against specific target cell expressed epitopes.

These and other objects and advantages of the invention will become more readily apparent from the following detailed description of the invention when taken in conjunction with the accompanying drawings, in which:

BRIEF DESCRIPTION OF THE DRAWINGS

FIG. 1 is a side elevation view of a blood sample tube and insert assembly which can be utilized to perform the procedure of this invention;

FIG. 2 is a schematic view of an automated microscopocal instrument assembly which is adapted for use in conjunction with the paraphernalia of FIG. 1 to perform the procedure of this invention;

DETAILED DESCRIPTION OF THE INVENTION

Figure 3:
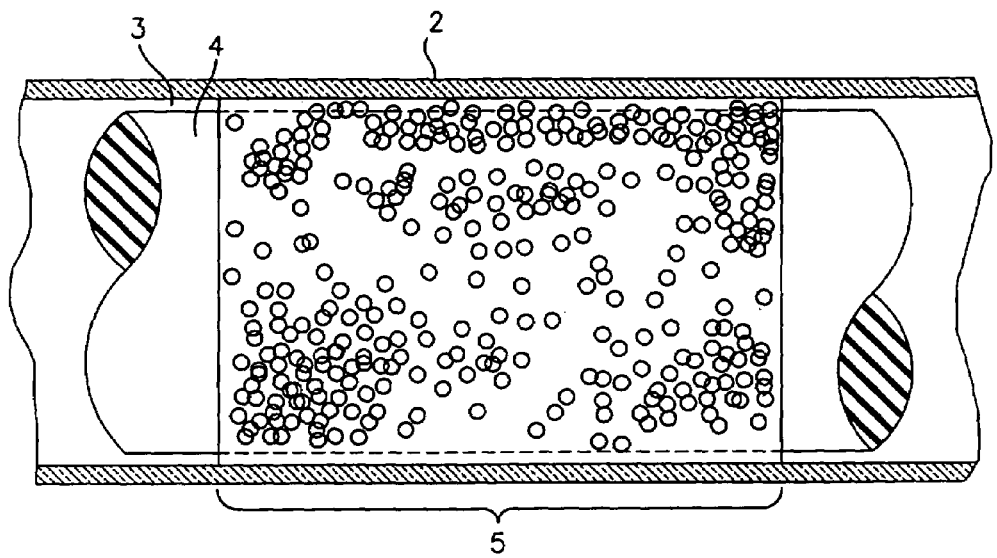
FIG. 3 is a graphic depiction of the lymphocyte/monocyte layer of blood cells which form in the buffy layer of the centrifuged blood sample which blood cells are illuminated with a first wavelength of light.

Referring now to the drawings, there is shown in FIG. 1 a side elevational view of a sampling tube and and insert assembly, which is referred to hereinafter generally as "the paraphernalia" and which includes a transparent blood sampling tube 2 that contains an elongated plastic insert 4. The tube 2 has an upper end 6 which is closed off by means of a closure cap 10. The tube 2 is a larger tube which is sized to contain about 10 mls of blood. The thickness of the gap between the tube bore and the insert 4 will be larger than the diameter of the target cells, and preferably will be equal to or less than the depth of the field of view of the detection instrument which is described in greater detail hereinbelow. The gap between the tube bore and the insert 4 will thus be accessible to target cells and the cells will be viewable in the gap by the detection instrument's optics. Generally, the red blood cells will be found in the section of the centrifuged blood sample labeled "RBC", the white blood cells will be found in the section labeled "WBC", and the plasma will be found in the section labeled "PL".

FIG. 2 is a schematic depiction of an automated colorimetric microscopocal instrument assembly, which is denoted generally by the numeral 12, and which can be used to scan a centrifuged blood sample that is contained in the paraphernalia shown in FIG. 1, and can, without human intervention, colorometrically differentiate between labeled target cells and other non-target cells in the layers being scanned, and can create and store, or can transmit an image of the cell layers being scanned to a remote site where the images can be analyzed. The instrument assembly 12 includes a stage 14 which includes at least one rotatable support 16 that engages the ends of the sample tube 2 and enables the sample tube 2 to be rotated about its axis as the contents of the tube 2 are scanned. A reversible electric motor 18 selectively rotates a drive screw 20 in opposite directions so that the tube 2 can be axially moved in one direction and then in the reverse direction as the tube 2 is rotated stepwise in the stage 14. In this manner, the entire circumferential contents of the tube 2 in the area thereof of interest can be scanned. The automatic embodiment of the instrument assembly 12 includes a CCD camera 22 which, by means of a beam splitter 24 and lens 26, is focused upon the annular sample-containing gap in the tube assembly 2, which gap is located between the tube bore wall and the outer surface of the insert 4. It will be appreciated that the operating range of the lens 26 is preferably at least equal to the thickness of the gap between the tube bore and the insert 4 in the tube 2, and that the lens 26 can be moved toward and away from the tube 2 so as to adjust the focus of the instrument. Although it is preferable that the entire expanded layer be in focus, examination of the layer can also be performed by imaging and then analyzing multiple focal planes within the layer. This has the advantage of being able to capture greater detail at the expense of requiring an increased number of images. The useful depth limit of the expanded layer is determined by the depth at which a usable image cannot be gathered due to light scatter by the thickness of the material over the target cells.

The CCD camera 22 views and records images of the sample through a plurality of different emission light wave filters 28, 30 and 32 which, for example, may be mounted on a selectively rotatable filter wheel 34. The instrument assembly 12 also includes an excitation light source 35 which directs an excitation light beam at the sample tube 2 through the beam splitter 24 and the focusing lens 26. A series of excitation light wave length filters 36, 38 and 40 may, for example, be mounted on a second selectively rotatable filter wheel 42. The excitation light beam is deflected by the beam splitter 24 toward the focusing lens 26, and is focused on the sample tube 2 by the lens 26. Thus, the two filter wheels 34 and 42 allow one to selectively control and vary the wave length of the excitation light source, as well as the emitted light source. A preprogrammed processor controller 44 is operable to selectively control the rotation of the sample tube 2, the rotation of the filter wheels 34 and 42, and operation of the CCD camera 22. The controller 44 thus enables fully automatic operation of the instrument assembly 12 without the need of human intervention.

Alternatively, the analysis of the blood sample may be performed by the use of a pixel-by-pixel spectrographic examination of transmitted or reflected light, where the target cells are detected by the difference in their spectral "signature" compared to the spectral signatures of adjacent blood cells. There will be a difference between the various cells due to the innate coloration or colorants used in place of the epitope-specific fluorescent labels. The alternative approach has the advantage of decrease instrument complexity. Instruments of the latter type can be procured from Cambridge Research & Instrumentation, Inc., Wobum, Mass.

The instrument assembly 12 operates in the following manner to capture and record images of the results of scanning the blood sample contained in the tube 2 for highlighted target cells, and also for confirming the labeled nature of observed target cells in situ in the blood sample. A sample of anticoagulated whole blood is drawn into the sampling tube 2 and insert 4 assembly. The blood sample will be admixed in the tube 2, or prior to being drawn into the tube 2, with a solution of labeled antibodies which are directed against abnormal epitopes which are expressed from within the target cells due to the diseased or other unusual internal makeup of the target cells. The blood sample may also be admixed with a non-specific stain such as acridine orange (AO) which will differentially highlight the various subsets of white cells and the platelets in the blood sample, and well as any white cell fragments which may be in the blood sample.

Figure 4:
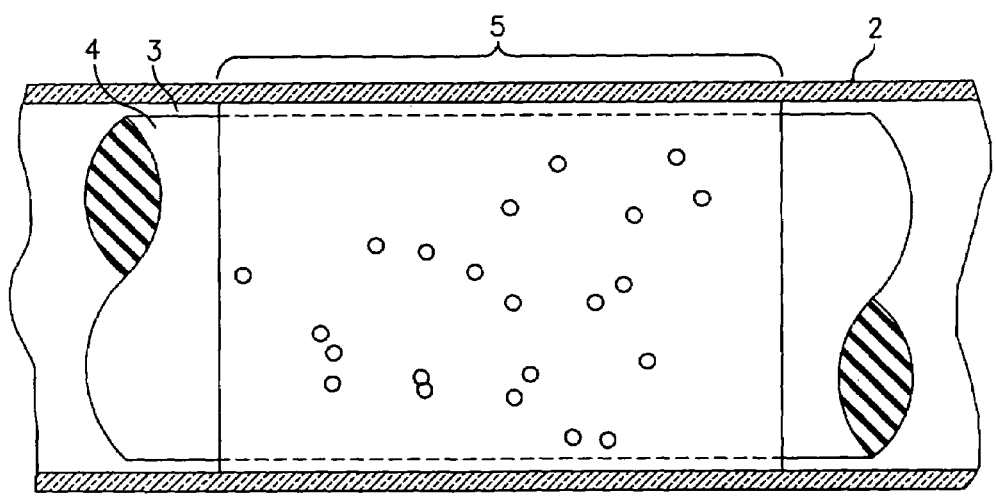
FIG. 4 is a graphic depiction of the same area in the blood sample wherein the blood cells are illuminated with a second wavelength of light which causes the target cell epitope label to fluoresce or otherwise be differentiated.

Referring now to FIGS. 3 and 4 there are shown consecutive images of an area 5 of a centrifuged blood sample which is being scanned by the system of this invention for the presence or absence of target infected, or otherwise rare event, blood cells. The area in question in this case is the area of the buffy layer in the centrifuged blood sample wherein the lymphocyte and monocyte cells will gravitate.

It will be noted, as observed above, the insert 4 and the tube 2 combine to create a narrow annular gap 3 into which the target cells, if present in the blood sample, will be located. The area 5 will be known to contain the lymphocyte and monocyte blood cells due to their known specific gravity or density. The AO stain will highlight all of the lymphocytes and monocytes present in the area 5, as shown in FIG. 3, when the area 5 is illuminated with a first wavelength light beam which excites the AO stain. The lymphocyte and monocyte-characteristic signal emanating from the area 5 confirms the location of the lymphocytes and monocytes in the centrifuged blood sample for the instrument 12 or for a technician visually surveying the blood sample. Once the lymphocyte/monocyte area 5 is located in the tube 2, the wavelength of the light beam illuminating the area 5 is changed to a second wavelength which is operative to excite the label which has been coupled with the expressed epitope-specific labeled binding materials. If any target cells are present in the area 5, the image that will be produced is such as that shown in FIG. 4. Alternatively, in the event that it is not important to know in which cell layer target cells may reside, the first fluorescent wavelength light source can be dispensed with, and the search for target cells can be carried out within the entire expanded area of the blood sample using only an excitation/emission wavelength light source combination which is suitable for the specifically labeled target epitope.

As noted in FIG. 4, some of the lymphocytes and/or monocytes will be highlighted in the area while the rest of the cells that were previously highlighted will not be seen under the second wavelength illumination. The highlighted cells shown in FIG. 4 are cells that have the expressed target epitope and thus are target cells which qualify as target rare events. As previously noted, these cells could be virally infected cells, or some other rare event cells. If there are no target cells in the area 5, then the image that would be shown in FIG. 4 would be blank, and show no highlighted cells.

The following is a list of examples of specific conditions which express surface antigens on target cells.

(1) Lymphocytes (target cells) which have been infected with HIV-1 will express a gp120 protein epitope on the surface of the infected cells within three days of having been infected. This expressed epitope can be detected with a solution containing fluorescently-tagged monoclonal antibodies, or other labeled binding materials, that are directed against the gp120 epitope, which solution is admixed with the whole blood sample.

(2) Blood cells (target cells) which have been infected with CMV will express virus-specific glycoproteins and antigens of this herpes virus on the surface of the infected cells within one day of having been infected. These expressed antigens can be detected with a solution containing fluorescently-labeled monoclonal antibodies, or other labeled binding agents that are directed against the antigens in question, which solution is admixed with the whole blood sample.

(3) Lymphocytes (target cells) which have been infected with HCV will express various protein epitopes on the surface of the infected cells in patients with chronic HCV infection. These expressed epitopes can be detected with a solution containing a mixture of labeled monoclonal antibodies, such as 4,6E7-F6; 1,4G11-B4G10; 2C4G3; 22A5B12; and 20A6F3, for example, that are directed against the various HCV-specific epitopes, which solution is admixed with the whole blood sample.

(4) Lymphocytes which have been infected with EBV will express an EBV-specific antigen on the surface of the infected cells. This expressed antigen can be detected with a solution containing labeled B532 monoclonal antibodies that are directed against the expressed antigen, which solution is admixed with the whole blood sample.

(5) Mammalian blood cells contain Major Histo Compatibility (MHC) gene complexes which encode surface membrane antigens (epitopes) that are unique to the host blood donor. In human beings, lymphocytes and other blood cells express MHC gene complexes known as human leukocyte antigens ("HLA" epitopes). These epitopes are recognized by commercially available monoclonal antibodies. Foreign cells (target cells) can be identified in the host's blood when target cell epitopes are present which target cell epitopes differ from the host's unique surface epitopes. For example, a woman may have the HLA epitopes A2; A36; B22; B53; DR8; DR9; DQ1; and/or DQ4. If her mate's epitopic phenotype is A3; A36; B22; B59; DR1; DR10; or DQ2, then fetal cells can be detected and quantified in her blood during pregnancy by identifying circulating cells with any or all of the unique paternally-derived antigens (A3; B59; DR1; DR10; or DQ2). This information can be helpful in evaluating maternal fetal hemorrhage or in prenatal diagnostics where fetal cells are harvested for genetic analysis.

Similarly, if the woman in question were to receive a bone marrow transplant, donor cells could be identified and quantified in her blood by identifying circulating cells with unique donor antigens. The same procedure could be used for a male recipient. This information would be of value in assessing engraftment or organ transplant problems which are generally characterized as graft-vs-host disease. In graft-vs-host disease, the graft or transplant donor's leukocytes from the graft or transplant may multiply in the host's body to the extent that the donor's leukocytes will begin to attack the host's body and can cause health problems.

It will be readily appreciated that the procedure of this invention can be used to detect and enumerate target blood cells in situ, in a sample of anticoagulated whole blood. The blood sample is contained in a transparent sampling container which can be centrifuged and which may contain about 10 mls of blood. The sampling container contains an insert which will force the target blood cells into a restricted volume viewable space inside of the container. The insert is preferably a plastic float that will settle into the red blood cell layer when the blood sample is centrifuged and will extend through the buffy coat (white cell) layer so as to axially expand the length of each of the white cell subsets in the buffy coat layer, and also at least a portion of the red cell layer. The procedure of this invention can be performed in a sealed container assembly that protects laboratory technicians against exposure to the blood sample. Furthermore, the procedure of this invention can be completed in a relatively short period of time so as to obtain test results within, at most, a matter of several hours or less.

Since many changes and variations of the disclosed embodiments of the invention may be made without departing from the inventive concept, it is not intended to limit the invention otherwise than as required by the appended claims.

What is claimed is:

1. A method for detecting circulating target fetal blood cells in a sample of a pregnant female donor's blood, which target fetal cells express human leucocyte antigens (target HLA epitopes) that differ from the donor's unique HLA epitopes, said method comprising the steps of:
   a) providing a transparent container having a cavity containing an insert said container and insert combining to form a free volume between the insert and a wall or walls of the container;
   b) combining the blood sample with one or more target HLA epitope specific labeling agents so as to colorimetrically differentiate any individual target cells in the blood sample from other cells in the blood sample;
   c) placing the blood sample in the container and centrifuging the blood sample in the container so as to cause any individual target cells present in the blood sample to localize in said free volume in the container;
   d) examining the centrifuged blood sample for the presence or absence of any individual differentiated target cells found in situ in the free volume in the container; and
   e) said combining step being performed either before or after the blood sample is placed in the container.

2. A method for detecting circulating target donor blood cells in a sample of a sample of a recipient's blood, which target donor cells express human leucocyte antigens (target HLA epitopes) that differ from the recipient's unique HLA epitopes, said method comprising the steps of:
   a) providing a transparent container having a cavity containing an insert, said container and insert combining to form a free volume between the insert and a wall or walls of the container;
   b) combining the blood sample with one or more target HLA epitope specific labeling agents so as to calorimetrically differentiate any individual target donor cells in the blood sample from recipient blood cells in the blood sample;
   c) placing the blood sample in the container and centrifuging the blood sample in the container so as to cause any individual target cells present in the blood sample to localize in said free volume in the container;
   d) examining the centrifuged blood sample for the presence or absence of any individual differentiated target cells found in situ in the free volume in the container; and
   e) said combining step being performed either before or after the blood sample is placed in the container.

3. A method for detecting circulating target leukocyte blood cells in a sample of a transplant or graft recipient's blood, which target leukocyte cells express human leukocyte antigens (target HLA epitopes) that differ from the recipients unique HLA epitopes, said method comprising the steps of:
   a) providing a transparent container having a cavity containing an insert, said container and insert combining to form a free volume between the insert and a wall or walls of the container;
   b) combining the blood sample with one or more target HLA epitope specific labeling agents so as to calorimetrically differentiate any individual target leukocyte cells in the blood sample from other leukocyte cells in the blood sample;
   c) placing the blood sample in the container and centrifuging the blood sample in the container so as to cause any individual target leukocyte cells present in the blood sample to localize in said free volume in the container;
   d) examining the centrifuged blood sample for the presence or absence of any individual differentiated target leukocyte cells found in situ in the free volume in the container; and
   e) said combining step being performed either before or after the blood sample is placed in the container.

* * * * *